United States Patent [19]

Temin et al.

[11] Patent Number: 4,980,289
[45] Date of Patent: Dec. 25, 1990

[54] PROMOTER DEFICIENT RETROVIRAL VECTOR

[75] Inventors: Howard M. Temin; Joseph P. Dougherty, both of Madison, Wis.

[73] Assignee: Wisconsin Alumni Research Foundation, Madison, Wis.

[21] Appl. No.: 43,000

[22] Filed: Apr. 27, 1987

[51] Int. Cl.⁵ .................... C12P 21/00; C12N 15/00; C12N 7/00
[52] U.S. Cl. .................. 435/235; 435/69.1; 435/70.1; 435/70.3; 435/172.1; 435/172.3; 435/252.3; 435/320; 435/240.1; 935/22; 935/23; 935/32; 935/52; 935/57
[58] Field of Search .................. 435/68, 70, 91, 320, 435/172.3, 240.1, 235; 536/27; 935/32, 34, 57, 60, 72, 70

[56] References Cited

U.S. PATENT DOCUMENTS 4,650,764  3/1987  Temin et al. .................. 435/240

OTHER PUBLICATIONS

Wagner et al., (1985) in *CSHSQB*, vol. 50: 691-700.
S. Yu et al., 83 Proc. Natl. Acad. Sci. USA, 3194-3198 (1986).
R. Cone et al., 7 Mol. Cell. Biol., 887-897 (1987).
E. Benz, Jr., 288 Nature, 665-669 (1980).
H. Temin, 28 Cell, 3-5 (1982).
K. Shimotohno et al., 26 Cell, 67-77 (1981).
L. Gritz et al., 25 Gene, 179-188 (1983).
J. Dougherty et al., 6 Mol. Cell. Biol., 4387-4395 (1986).
P. Southern et al., 1 J. Mol. Appl. Genet., 327-341 (1982).
M. Wickens et al., 226 Science, 1045-1051 (1984).
M. Emerman et al., 39 Cell, 459-467 (1984).
S. Watanabe et al., 79 Proc. Natl. Acad. Sci. USA, 5986-5990 (1982).
F. Graham et al., 52 Virology, 456-467 (1973).

Primary Examiner—Richard A. Schwartz
Assistant Examiner—Anne Brown
Attorney, Agent, or Firm—Quarles & Brady

[57] ABSTRACT

A recombinant retrovirus vector is disclosed. It is of the type having a normally replication incompetent retrovirus gene sequence with a foreign eukaryotic gene to be expressed. The retrovirus gene sequence is designed so as to be promoter deficient in the right side LTR. The vector can produce progeny virus from helper cells, which progeny can infect a eukaryotic host cell, form a provirus, and express the eukaryotic gene in the host cell. However, the provirus will then be defective in the retrovirus promoter, such that retrovirus RNA is not expressed from the provirus.

6 Claims, 3 Drawing Sheets

RETROVIRUS REPLICATION

RETROVIRUS VIRION

PROMOTER DEFICIENT RETROVIRAL VECTOR

BACKGROUND OF THE INVENTION

A. Field of the Invention

The present invention relates to recombinant DNA technology. It is especially useful in allowing the safe introduction of foreign DNA into eukaryotic cells.

B. Description of the Art

There has been much interest in introducing foreign DNA into eukaryotic cells. One reason for this interest is that some genetically caused diseases may be curable by introducing the foreign DNA into the cells, and allowing the foreign DNA to express a protein that the genetically defective cell cannot express. Another reason for this interest is that certain eukaryotic cells may prove to be the most suitable hosts for the production of certain eukaryotic proteins. Yet another reason is that this may permit farm animals to be genetically improved.

A promising approach for achieving the introduction of foreign DNA into eukaryotic cells was disclosed in an article by K. Shimotohno et al., 26 Cell 67–77 (1981). (The disclosure of this article and of all other articles and patents cited in this application are incorporated by reference herein as if fully set forth). This approach used plasmids with retrovirus portions for growing up a stock of virus, and then used the progeny virus as a carrier for introducing foreign DNA into the vertebrate cell genome.

These "retrovirus vectors" were designed so as to be defective with respect to the expression of certain retrovirus structural genes. Thus, by themselves they were replication defective. They could, however, be replicated (packaged) to grow up a stock of the virus by using DNA virus of helper cells.

One type of helper cell contained helper virus DNA that supplied the missing viral gene products. The helper virus DNA itself was encapsidation-minus, so its RNA was not packaged. By using this helper cell, pure virus stock could be obtained which did not contain helper virus. See generally U.S. Pat. No. 4,650,764, issued Mar. 17, 1987 to Temin et al.

One theoretical problem with such systems is that because of their design it is conceivable that an endogenous retrovirus (e.g. one already in a host) could act as a pseudo helper virus. Thus, after infecting a host with the virus, the virus could replicate in the host (and cause disease). Another problem is that a promoter sequence present in the provirus that is formed after infection of the host might trigger cellular gene sequences (leading to side effects such as perhaps cancer).

Thus, it can be seen that a need exists for a retrovirus vector that can be replicated in a helper cell to produce progeny virus that will infect an eukaryotic host, but is designed so that the resulting provirus will be promoter deficient. Ideally, such a system should also be designed to reduce the risks of recombination and permit efficient expression of the foreign gene of interest.

SUMMARY OF THE INVENTION

One embodiment of the present invention is a recombinant retrovirus vector of the type having a normally replication incompetent retrovirus gene sequence with a foreign eukaryotic gene. The improvement relates to having the retrovirus gene sequence made with a deficiency in the retrovirus promoter such that the vector can still produce progeny virus in a helper cell, with the progeny virus being capable of infecting a selected eukaryotic host cell, forming a provirus, and expressing the eukaryotic gene in the host cell; but the provirus will be defective in the retrovirus promoter sequence. Preferably, the vector is a recombinant plasmid.

In an especially preferred form, a foreign internal promoter is positioned adjacent to the foreign eukaryotic gene on the vector so as to permit expression of the foreign eukaryotic gene in the eukaryotic host cell without initiating retroviral provirus gene expression. In one form, the reading direction of the foreign promoter is inverted relative to the normal reading direction of the retrovirus gene sequence, and a foreign 3' RNA processing sequence is positioned on the side of the foreign eukaryotic gene sequence which is opposite to the foreign promoter.

An alternative preferred embodiment relates to a normally replication incompetent retrovirus of the type having a retrovirus portion and a foreign eukaryotic portion, the retrovirus portion having a deficient promoter portion, such that the virus is capable of infecting a eukaryotic host cell, forming a provirus, and expressing a eukaryotic protein coded for by the foreign eukaryotic portion in the host cell, but the provirus will be defective in a retrovirus promoter such that retroviral provirus gene expression doesn't take place in the host cell.

The present invention allows one to select a eukaryotic gene of interest, insert it into a vector designed in accordance with the present invention, transfect a helper cell with the vector using standard techniques, harvest virus stock from the helper cell using standard techniques, use the harvested progeny virus to infect a target cell using standard techniques, and have the proviruses which are formed in the target cells express the inserted eukaryotic gene, but without expressing any retroviral proteins. Since there is no retroviral promoter that is active on the provirus, endogenous helper proteins cannot trigger production of a virus from the provirus Also, since there is no gene of interest, insert it into a vector designed in accordance with the present invention, transfect a helper cell with the vector using standard techniques, harvest virus stock from the helper cell using standard techniques, use the harvested progeny virus to infect a target cell using standard techniques, and have the proviruses which are formed in the target cells express the inserted eukaryotic gene, but without expressing any retroviral proteins. Since there is no retroviral promoter that is active on the provirus, endogenous helper proteins cannot trigger production of a virus from the provirus. Also, since there is no retroviral promoter in the provirus, the provirus cannot provide a retrovirus signal that might trigger the host cell to act in an unintended way. The lack of retroviral promoter stops production of retroviral RNA. This system renders much more likely the acceptability of recombinant retrovirus as drugs for vertebrates.

The objects of the present invention therefore include:

a. providing a retrovirus vector of the above kind which can be used to produce a stock of normally replication incompetent recombinant retrovirus, with the progeny being capable of infecting a host cell and forming a provirus, where the provirus is capable of expressing a foreign eukaryotic gene but not retrovirus RNA; and b. providing a progeny virus of the above kind.

These and still other objects and advantages of the present invention will be apparent from the description which follows In the description, the preferred embodiments of the invention will be described with reference to the accompanying drawings. These embodiments do not represent the full scope of the invention. Rather, the invention may be employed in other embodiments. Reference should therefore be made to the claims to interrupt the breath of the invention.

DESCRIPTION OF THE PREFERRED EMBODIMENTS

Figure 1:
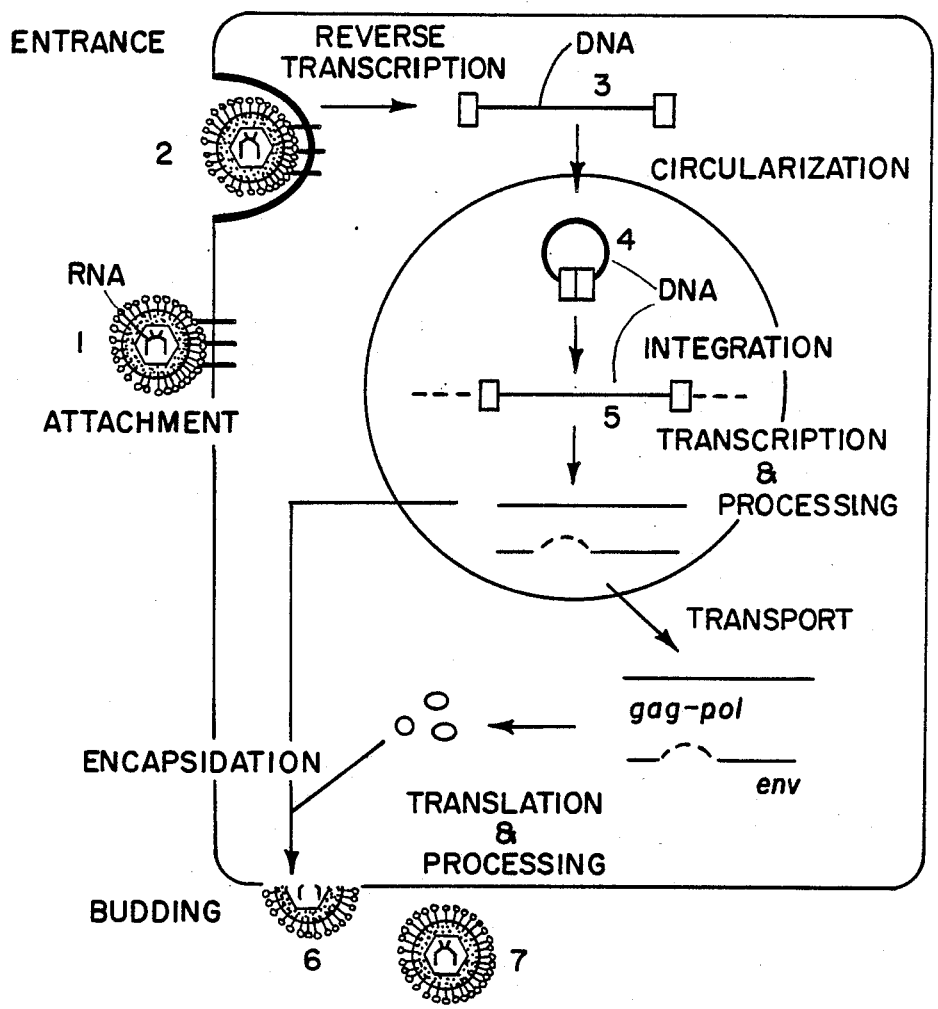
FIG. 1 depicts in schematic form the life cycle of spleen necrosis (SNV) retrovirus.
Figure 2:
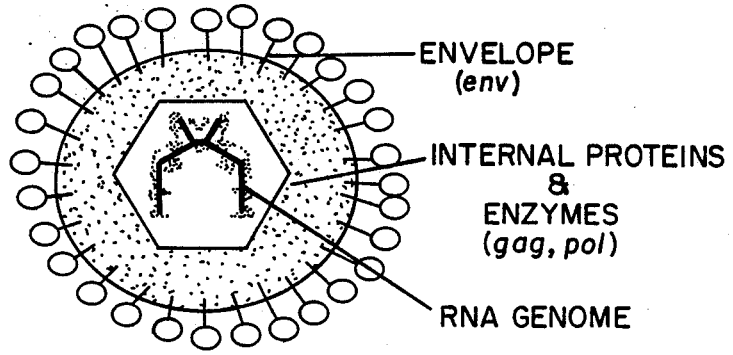
FIG. 2 shows the structure of an SNV retrovirus.

The life cycle and structure of a typical retrovirus is depicted in FIG. 1 of the drawings. The virus particle 1 carries the genetic message in RNA form. It attaches to the outer wall of a cellular host 2. After inserting itself into the cell, its RNA is reverse transcribed so as to form a DNA version 3 of the genetic sequence The DNA then circularizes 4 and integrates into the cellular genome to form a "provirus" 5. The provirus is transcribed to provide the RNA which then forms the virus structure 6, and new virus particles 7 bud out of the cell.

Figure 3:
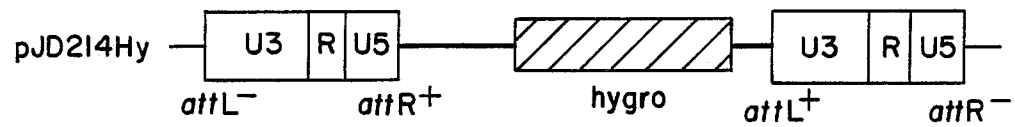
FIG. 3 shows relevant portions of a series of pBR322 derivative plasmid vectors.
Figure 3:
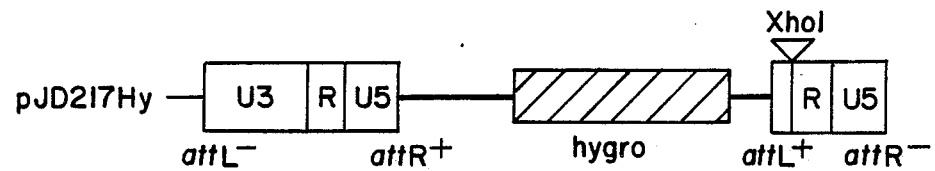
Figure 3:
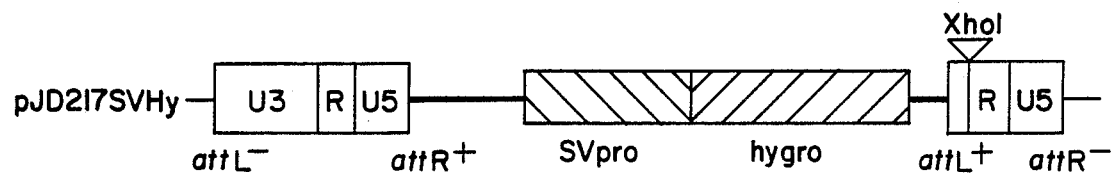
Figure 3:
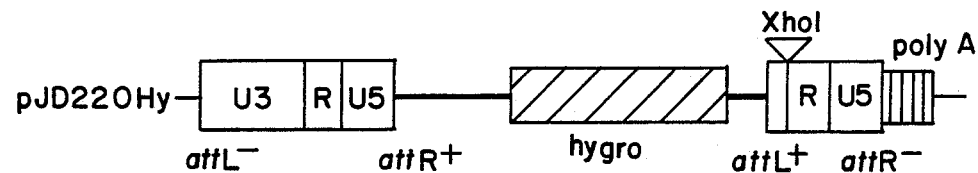
Figure 3:
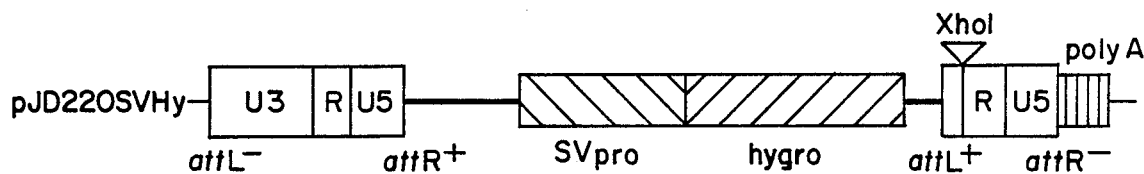
Figure 4:
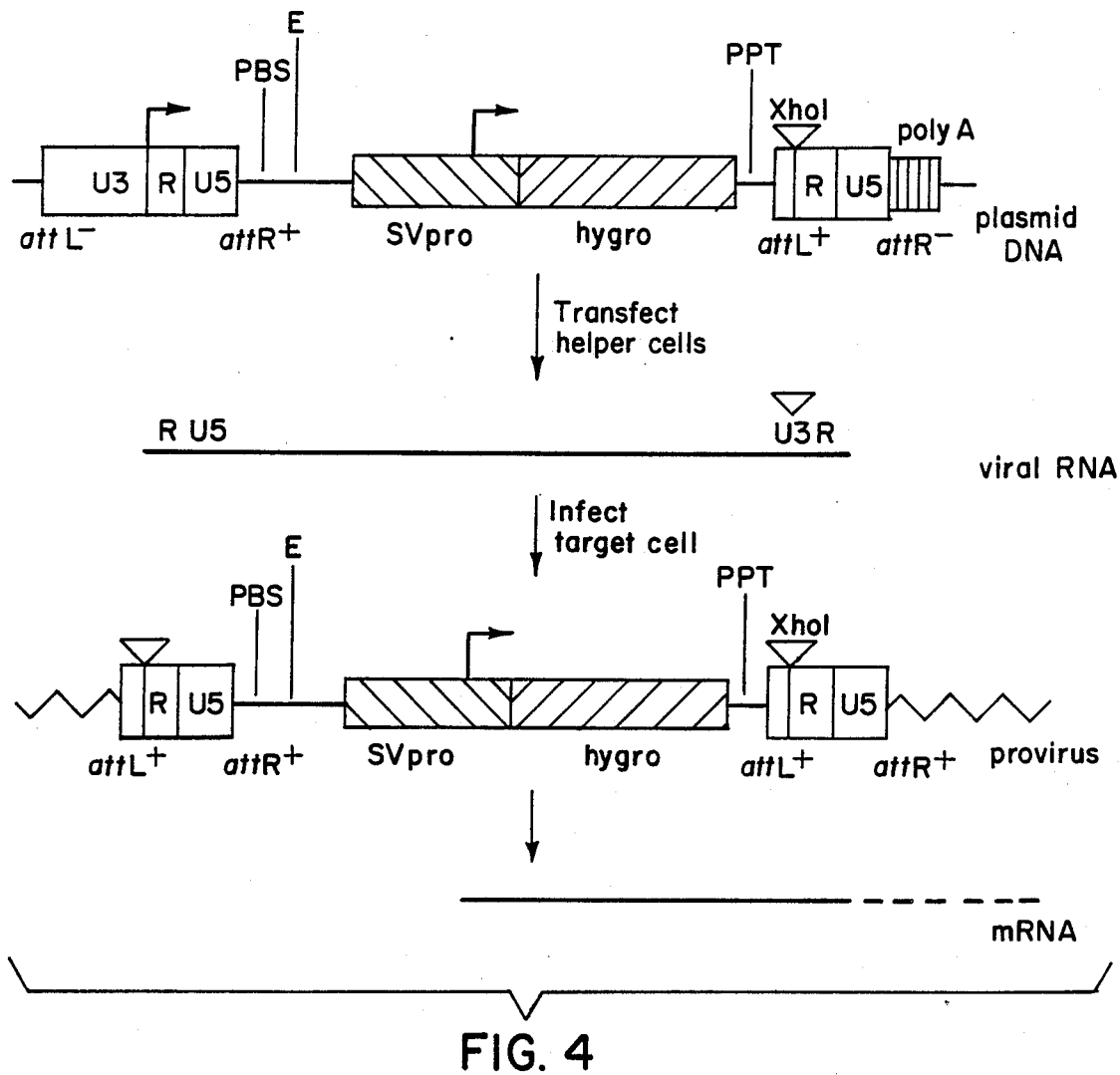
FIG. 4 shows how a vector of the present invention can be used.
Figure 5:
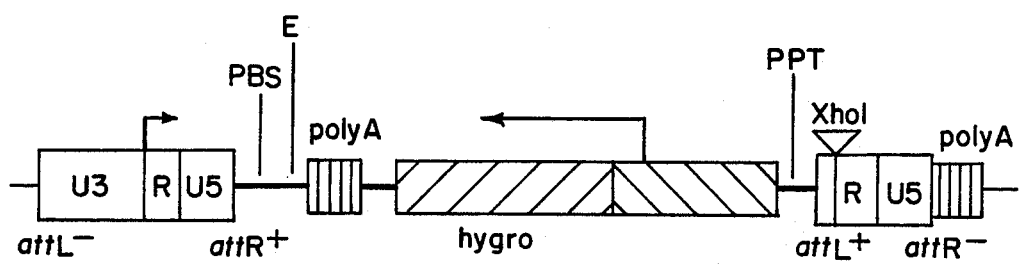
FIG. 5 shows an alternative embodiment, pRD8, of the present invention.

In FIGS. 3-5, the boxes with right leaning diagonal lines represents a selected foreign gene sequence, hygromycin. The boxes with left leaning diagonal lines represent the SV40 promoter. The boxes with vertical lines are foreign poly-(A) (polyadenylation) sites. Transcription initiation sites and directions are indicated by arrows. The open boxes with U3, R, and U5 represent long terminal repeat (LTR) sequences with retroviral promoter sequences. The inverted triangles represent a deleted promoter with an XhoI linker insertion. The thin outside lines represent pBR222. The jagged outside lines represent cellular chromosomal sequences.

Abbreviations that are used are pro - promoter, enh - enhancer, PBS - primer binding site for DNA synthesis, PPT polypurine track for DNA synthesis, E - encapsidation sequences for RNA packaging, attR+—a sequence that will form the right side of the attachment site relating to integration, attL+—the sequence that will form the left site of the attachment side relating to integration, attL⁻—the deletion of the original provirus left-side attachment site, and attR⁻—the deletion of the original right side attachment site.

FIG. 3 shows various spleen necrosis virus (SNV) retrovirus recombinant DNA sequences as part of pBR322 plasmid vectors. "Hygro" refers to a hygromycin resistance gene as reported in L. Gritz et al., 25 Gene 179-188 (1983) which supplies resistance to hygromycin (and thus can also act as a selection marker during experiments).

pJD214, a precursor not depicted, consists of a left hand LTR of SNV without its left hand attachment site, coordinates 10 to 861, which also includes the PBS and E. It then contains a pUC12 linker (Pharmacia) which contains Sac 1, Sma 1, Xma 1, BamH 1, Xba 1, Sal 1, Pst 1, and Hind III cleavage sites. There then is a Cla I site and a right hand LTR from 7691 to 8267, lacking its right hand attachment site. pJD214Hy is described in J. Dougherty et al., 6 Mol. Cell Biol. 4387-4395 (1986). The hygromycin gene was inserted into the Hind III site of pJD214 as described there. The advantages of this pJD214 Hy vector are that it has the minimum amount of retrovirus sequences and the extra attachment sites were removed so there could not be recombination between them.

pJD217SVHy was made by deleting the SacI-AvaI fragment (SNV map unit 7.747 to 8.127) from the right-side LTR and replacing it with an XhoI linker. This procedure resulted in a deletion of the entire "U3" sequence, except for 10 bp at the 5' prime end, which includes the left-side attachment site attL. It should especially be noted that for this construction, in the left side LTR the 10 bp of U3 remaining in the right side LTR were deleted. Thus, there is no homology between the two U3's on the left side and right sides, and the risk of recombination is reduced.

pJD217SVHy was constructed by inserting the 565 bp NdeIHindIII fragment from pSV2-neo (See P. J. Southern et al., 1 J. Mol. Appl. Genet 327-341 (1982)) containing the SV40 early promoter into the XbaI site of pJD217Hy.

pJD220Hy was made by inserting the 220 bp BamHI-HindIII fragment containing the SV40 polyadenylation site (See M. Wickens et al., 226 Science 1045-1051 (1984)) into the BamHI site at the 3' prime end of U5 in pJD217Hy.

pJD220SVHy was constructed by inserting the 220 bp BamHI-HindIII fragment into the BamHI site of pJD217SVHy.

Techniques and Materials

All constructions were made by using standard recombinant DNA techniques. See generally T. Maniatis et al., Molecular Cloning: A Laboratory Manual, Cold Spring Harbor (1982). D17 dog cells and D17-C3 dog helper cells were grown as previously described. See generally M. Emerman et al. 39 Cell 459-467 (1984); S. Watanabe et al., 79 Proc. Natl. Acad. Sci. USA 5986-5990 (1982). The D17-C3 dog cell line is a D17 helper cell line that supplies trans-functions for packaging of defective retrovirus vectors without production of replication competent helper virus. Selection for hygromycin-resistant cells was done in the presence of 100 ug/ml hygromycin (Eli Lilly).

Transfections were done by the calcium phosphate precipitation method. See generally F. Graham et al., 52 Virology 456-467 (1973). Virus titers were obtained as described in M. Emerman et al., 39 Cell 459-467 (1984).

Deposits of pJD220SVHy and the FIG. 5 pRD8 in D17 host dog cells have been made with the American Type Culture Collection, Rockville, Md., as ATCC Nos. 67393 & 67394 respectively. Samples from the deposits are available in accordance with U.S. patent law requirements and the requirements of any applicable foreign patent laws upon issuance of the patent. No patent license is intended by such availability.

Rationale of the Invention

FIG. 4 diagrams the basic rationale of the invention. The enhancer and the promoter sequences of the retrovirus (which are present at U3 in SNV) have been deleted from only the right side of the DNA sequence in the plasmid vector. The total lack of homology in the two U3 sequences prevent recombination. The vector DNA is used to transfect helper cells in a conventional manner Because transcription from the vector begins at R on the left side, and because the U3 promoter on the left side is not defective, virus can be harvested from the transfected helper cell in the conventional manner. Target cells can then be infected with the harvested virus.

Since the right side U3 supplies the coding sequences for both U3 segments in the resulting provirus, the transcriptional promoter which was originally deleted only on one side of the plasmid DNA shows up as being deleted from both sides in the resulting provirus. The vector therefore permits a stock of the retrovirus progeny virus to be grown up, yet will not permit further replication after one infection cycle. This occurs automatically.

In FIG. 4 the hygromycin resistance gene is used as the foreign gene. However, it will be appreciated that eukaryotic genes of choice can be inserted at that position instead.

Returning now to FIG. 3, it should be noted that pJD217Hy does not contain an internal promoter to drive expression of the hygro gene in target cells. Thus, pJD217SVHy was formed in which the right side LTR enhancer and promoter have been deleted add the SV40 promoter is inserted next to the hygro gene so as to permit transcribing of the hygro gene in the D17 target cells. More sophisticated internal promoters (e.g. those inducible by heat or chemicals) can be inserted instead.

If an internal promoter is not inserted, there will be no promoter to produce the desired foreign eukaryotic gene expression. Preferably such a promoter is positioned immediately adjacent to the foreign eukaryotic of interest so that no intervening retrovirus genes RNA is expressed. Thus, the internal promoter in pJD220SVHy is placed 3' to the left side R, attR, PBS, and E. These sequences are essential for virus replication and will not be transcribed in the target cell if the internal promoter is so positioned.

It has been discovered that even pJD217SVHy will not act as efficiently as desired because the deletion of U3 also turns out to delete a polyadenylation sequence containing sequences essential for 3' processing of viral RNA. This problem can be partially overcome as shown in pJD220SVHy with the provirus for JD220SVHy then has no 3' RNA processing sequence. This problem can be overcome by the structure shown in FIG. 5, where the poly-(A) sequence is also inserted so as to sandwich the hygro gene between the SV40 promoter and the poly-(A), with the promoter and poly-(A) sequence being in inverse reading order direction.

FIG. 5 (pRD8) is constructed from pJD220Hy by inserting a 3' RNA processing sequence between Sstl and Sal 1 sites, then removing the hygro gene and replacing it in the opposite direction with a promoter and the hygro gene.

It will be appreciated that the retroviral vector of the present invention has viral promoter signals that are not carried through to the progeny provirus. This lowers the risk that there will be spread of vector virus in an infected host, even in the remote event that there is endogenous helper virus. It also minimizes the likelihood that the promoter of the provirus will trigger side effects in the cell.

Because deletion of most of the U3 in SNV resulted in a loss of correct 3' end processing of viral RNA, even though AAUAAA was still present, a polyadenylation site was added to the vector. Moreover, problem recombinations are unlikely because the U3 sequences in the vector are not homologous.

EXAMPLE

Beginning with a virus stock recovered from transfection of pJD220SVHy in D17-C3 helper cells (harvested five days post-transfection) D17 dog cells were infected and selected for hygromycin-resistance. Those cells with hygromycin resistance had the desired provirus.

Xhol-digested genomic DNA from D17 cells infected with JD220SVHy should theoretically give a 2.2 kbp fragment if hybridized to hygro-specific sequences. To test this, we expanded individual D77 cell clones infected with JD220SVHy, isolated genomic DNA from the cell clones, digested the genomic DNA with Xhol, electrophoresed the DNA on a 1% agarose gel, blotted to nitrocellulose, and hybridized the blot with a hygro-specific probe. Analysis of genomic DNA from five different JD220SVHy infected D17 cell lines showed that each had a 2.2 kbp fragment when probed with a hygrospecific sequence.

The invention is believed to be applicable to retroviruses other than just SNV, as well as to a wide range of foreign eukaryotic genes and foreign promoters. As such, the illustrative embodiments described above do not represent the full invention. Instead, the scope of the invention is to be judged by the claims which follow.

We claim:

1. In a recombinant retrovirus vector having a 5' LTR, a 3' LTR, a promoter that can be recognized by a selected eukaryotic host cell, and a non-retroviral gene under the control of said recognized promoter, an improvement comprising:

the 5' LTR is positioned 5' of the non-retroviral gene and has a transcriptional promoter sequence and a viral integration point;

the 3' LTR is positioned 3' of the non-retroviral gene and has a viral integration point, a defective polyadenylation assistance sequence portion in the U3 region and a defective transcriptional promoter portion;

an exogenous polyadenylation addition signal sequence recognized by the selected host cell is positioned on the vector 3' to the 3' LTR viral integration point; and the recognized promoter is positioned adjacent to the non-retroviral gene on the vector so as to permit expression of the non-retroviral gene in the eukaryotic host cell;

whereby when constructed as described above the vector can still produce progeny virus in a helper cell with the progeny virus being capable of infecting the selected eukaryotic host cell and forming a provirus in the host cell, with the non-retroviral gene then being expressible in the host cell, but the provirus in the host cell will be replication incompetent even in the presence of a helper virus.

2. In a recombinant retrovirus vector having a 5' LTR, a 3' LTR, a promoter that can be recognized by a selected eukaryotic host cell, and a non-retroviral gene under the control of said recognized promoter, an improvement comprising:

the 5' LTR is positioned 5' of the non-retroviral gene and has a transcriptional promoter sequence and a viral integration point;

the 3' LTR is positioned in 3' of the non-retroviral gene and has a viral integration point, a defective polyadenylation assistance sequence portion, and a defective transcriptional promoter portion;

a first exogenous polyadenylation addition signal sequence recognized by the selected host cell is positioned on the vector 3' to the 3' LTR viral integration point;

a second exogenous polyadenylation addition signal sequence recognized by the selected host cell is positioned on the vector;

the recognized promoter is positioned adjacent to the non-retroviral gene on the vector so as to permit expression of the non-retroviral gene in the eukaryotic host cell; and the transcriptional orientation of the recognized promoter, non-retroviral gene, and second exogenous polyadenylation addition signal sequence is inverted relative to the transcriptional orientation of the 5' LTR transcriptional promoter and first exogenous polyadenylation addition signal sequence, and the second exogenous polyadenylation addition signal sequence is adjacent to the non-retroviral gene at the end of the non-retroviral gene that is opposite the end to which the recognized promoter is adjacent;

whereby when constructed as described above the vector can still produce progeny virus in a helper cell with the progeny virus being capable of infecting the selected eukaryotic host cell and forming a provirus in the host cell, with the non-retroviral gene then being expressible in the host cell, but the provirus in the host cell will be replication incompetent even in the presence of a helper virus.

3. A retrovirus that has been produced by the vector of claim 1.

4. A retrovirus that has been produced by the vector of claim 2.

5. A host cell containing the provirus of claim 1.

6. A host cell containing the provirus of claim 2.

* * * * *

UNITED STATES PATENT AND TRADEMARK OFFICE
CERTIFICATE OF CORRECTION

PATENT NO. : 4,980,289
DATED : December 25, 1990
INVENTOR(S) : Howard M. Temin; Joseph P. Dougherty It is certified that error appears in the above-identified patent and that said Letters Patent is hereby corrected as shown below:

| | |
|---|---|
| Column 2, Line 41 | Insert a "." after "provirus" |
| Column 3, Line 3 | Insert a "." after "follows" |
| Column 3, Line 29 | Insert a "." after "sequence" |
| Column 3, Line 48 | Insert a "-" after "PPT" |
| Column 4, Line 22 | Insert a "-" after "Ndel" |
| Column 6, Line 15 | "D77" should read --D17-- |
| Column 7, Line 1 | "in" should be deleted |
| Column 7, Line 3 | Insert "in the U3 region" after "portion" |

Signed and Sealed this

Sixth Day of October, 1992

Attest:

DOUGLAS B. COMER

Attesting Officer

Acting Commissioner of Patents and Trademarks